US00PP13458P2

(12) United States Plant Patent
Bradford

(10) Patent No.: US PP13,458 P2
(45) Date of Patent: Jan. 7, 2003

(54) PLUM TREE NAMED 'YUMMYGIANT'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/014,023

(22) Filed: Dec. 13, 2001

(51) Int. Cl.[7] ..... A01H 5/00

(52) U.S. Cl. ..... Plt./185; Plt./185

(58) Field of Search ..... Plt./184, 185

*Primary Examiner*—Bruce R. Campell
*Assistant Examiner*—W C Haas

(57) ABSTRACT

The present invention relates to a plum tree, *Prunus salicina,* and more particularly to a new and distinct variety broadly characterized by a medium size, vigorous, hardy, self-unfruitful, and productive tree. The fruit matures under the ecological conditions described approximately the second week in July, with first picking on Jul. 8, 2001. The fruit is uniformly large in size, excellent in flavor, round in shape, clingstone in type, firm in texture, yellow in flesh color, and mostly brownish red in skin color. The variety was developed from an open pollinated seed from an unnamed red plum.

1 Drawing Sheet

CROSS REFERENCE TO RELATED APPLICATIONS

This case is related to co-pending U.S. Plant patent application Ser. No. 10/014,024, filed Dec. 13, 2001, drawn to 'RED MAJESTY' plum.

BOTANICAL CLASSIFICATION

*Prunus salicina.*

BACKGROUND OF THE VARIETY

In a continuing effort to improve the quality of shipping fruits, I, the inventor, typically hybridize a large number of nectarine, peach, plum, apricot, and cherry seedlings each year. In an effort to exhibit recessive traits, I also grow a lesser number of open pollinated seeds of each of these fruits. In my breeding grounds during the summer of 1992 I regularly gathered open pollinated seeds from several different unpatented plum trees which bore red plums. This group of seeds, designated as "Red Plum (OP)", was germinated and grown as seedlings on their own root in my greenhouse and transplanted to a cultivated area of my experimental orchard at Bradford Farms near Le Grand, Calif. in Merced County (San Joaquin Valley).

The present invention relates to a new and distinct variety of plum tree, which has been denominated varietally as 'YUMMYGIANT'. It was selected by me during the 1997 fruiting season as a single plant from the group of open pollinated seedlings described above. Subsequent to origination and selection of the present variety of plum tree, I asexually reproduced it by budding and grafting in the experimental orchard described above, and such reproduction of plant and fruit characteristics were true to the original plant in all respects. The reproduction of the variety included the use of 'Nemaguard' Rootstock (unpatented) upon which the present variety was compatible and true to type.

The present variety is similar to 'Fortune' (unpatented) by producing red plums that harvest in July, but is distinguished therefrom and an improvement thereon by producing fruit that is larger in size, much sweeter in flavor, and matures about 8 days earlier. The variety blooms in the early season and is self-unfruitful, requiring cross pollination by other plums. Two acceptable pollinators are 'Ambra' (unpatented) and 'Autumn Rosa' (unpatented). Also, the variety produces an abundance of pollen, which attracts bees to facilitate the cross pollination.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif., and was developed when the fruit was firm ripe on Jul. 12, 2001, on the original tree during its ninth growing season. All major color code designations are by reference to the Inter-Society Color Council, National Bureau of Standards. Common color names are also used occasionally.

TREE

Size: Medium, reaching and maintaining a height of 14' [4.26 m] after nine growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Productive, thinning usually necessary.

Fertility: Self-unfruitful, requiring cross pollination by a suitable pollinator, such as 'Ambra' (unpatented) or 'Autumn Rosa' (unpatented).

Bearing: Regular bearer with no alternate being observed.

Trunk:

*Size.*—Medium, reaching a maximum diameter of 6" [152 mm.] after the ninth growing season.

*Texture.*—Somewhat shaggy.

*Bark color.*—Grayish brown [61. gy.Br].

*Lenticels.*—Few. Color: Brownish orange [54. brO]. Average Size: 5/16" [7.9 mm.].

Branches:

*Size.*—Diameter of scaffold is 2 3/8"[61 mm.] measured 12" above the crotch, typical of *Prunus salicina*, and dependent upon cultural practices and climatic conditions.

*Texture.*—Smooth on 1st year wood, increasing roughness with age.

*Color.*—1st Year Wood Topside: Deep brown [56. deep Br]. 1st Year Wood Underside: Moderate yellow green [120. m.YG]. Older wood: Deep yellowish brown [75. deep yBr].

*Lenticels.*—Medium in number. Color: Moderate orange yellow [71. m.OY]. Average Size: 1/16" [1.6 mm.].

Leaves:

*Size.*—Large. Average Length: 5" [127 mm.]. Average Width: 2¼" [57 mm.].

*Arrangement.*—Alternate.

*Thickness.*—Medium.

*Form.*—Elliptical.

*Apex.*—Acuminate.

*Base.*—Acute with an average angle of 80 degrees.

*Surface.*—Smooth.

*Color.*—Dorsal Surface: Moderate olive green [125. m.OlG]. Ventral Surface: Grayish yellow green [122. gy.YG].

*Margin.*—Finely serrate.

*Venation.*—Pinnately net veined.

*Petiole.*—Average Length: 5/8" [15.9 mm.]. Average Thickness: 1/16" [1.6 mm.]. Color: Light yellow green [119. l.YG].

*Stipules.*—Up to 2 per leaf, up to 8 per growing tip. Average Length: 3/16" [4.8 mm.]. Color: Moderate yellow green [120. m.YG] becoming Dark grayish reddish brown [47. d.gy.rBr] with age.

*Glands.*—Number: 2 to 4 per leaf. Position: Both alternate and opposite, positioned on the petiole and base of blade. Size: Small. Form: Globose. Color: Grayish reddish brown [46. gy.rBr].

*Leaf buds.*—Pointed.

Flower buds:

*Hardiness.*—Hardy, with respect to central California winters.

*Diameter.*—Typically 3/16" [4.8 mm.] 1 week before bloom.

*Length.*—Typically 3/8" [9.5 mm.] 1 week before bloom.

*Form.*—Not appressed.

*Surface.*—Pubescent.

*Color.*—White [263. White].

Flowers: Perfect, complete perigynous, usually a single pistil, typically twenty-four or more stamens, five sepals and petal locations alternately positioned.

*Number of flowers per cluster.*—1 to 9, average 5.

*Average flower diameter.*—13/16" [20.6 mm.].

*Number of petals.*—Five.

*Petal shape.*—Oval.

*Petal margin.*—Slightly wavy.

*Average petal diameter.*—5/16" [7.9 mm.].

*Average petal length.*—7/16" [11.1 mm.].

*Petal apex.*—Rounded.

*Petal base.*—Rounded, very wavy.

*Petal color.*—White [263. White].

*Anther color.*—Strong yellow [84. s.Y].

*Stigma color.*—Brilliant greenish yellow [98. brill. gY].

*Sepal color.*—Strong yellow green [117. s.YG] with rarely Grayish red [19. gy.R] tinge on the edges.

*Sepal length.*—5/32" [4 mm].

*Sepal width.*—5/32" [4 mm].

*Average pistil length.*—5/16" [7.9 mm.].

*Average stamen length.*—3/8" [9.5 mm.].

*Fragrance.*—Moderate when nectar is present.

*Blooming period.*—Early when compared with other varieties, 2 days after 'Ambra' in 2001.

*Onset of bloom.*—One percent on Feb. 15, 2001.

*Date of full bloom.*—Feb. 28, 2001.

*Duration of bloom.*—One to two weeks, dependent on ambient temperature.

FRUIT

Maturity when described: Firm ripe, Jul. 12, 2001.

Date of first picking: Jul. 8, 2001.

Date of last picking: Jul. 22, 2001.

Size: Uniform, large.

*Average diameter axially.*—2 5/8" [66.7 mm.].

*Average diameter across suture plane.*—2 5/8" [66.7 mm.].

*Typical weight.*—6.91 ounces [196 grams].

Form: Uniform, symmetrical, slightly oblong.

*Longitudinal section form.*—Oval to round.

*Transverse section through diameter.*—Round.

Suture: An inconspicuous line in a from the base to the apex located in a shallow groove near the apex becoming a sharper toward the base.

Ventral surface: Rounded.

Lips: Slightly toward the apex, slightly unequal.

Cavity: Flaring, suture showing on one side, strong greenish yellow [99. s.gY] stem markings typical.

*Depth.*—½" [12.7 mm.].

*Breadth.*—1" [25.4 mm.].

Base: Slightly cuneate to truncate.

Apex: Rounded.

Pistil point: A Moderate yellowish brown [77. m.yBr] dot.

Stem: Medium.

*Average length.*—7/16" [11.1 mm.].

*Average width.*—1/8" [3.2 mm.].

Skin:

*Thickness.*—Medium.

*Surface.*—Smooth.

*Tenacity.*—Tenacious to flesh.

*Astringency.*—Moderate.

*Tendency to crack.*—Slight in wet season.

*Color.*—Deep reddish brown [41. deep rBr] over a Moderate yellow [87. m.Y] background with Moderate yellow [87. m.Y] freckling throughout.

*Bloom.*—Abundant.

Flesh:

*Color.*—Light orange yellow [70. l.OY] from skin to stone.

*Surface of pit cavity.*—Light orange yellow [70. l.OY] fibers breaking when twisted from the stone.

*Amygdalin.*—Scarce.

*Juice.*—Abundant, rich.
*Texture.*—Firm, crisp.
*Fibers.*—Abundant, fine.
*Ripens.*—Slightly earliest toward the apex.
*Flavor.*—Low acid, very sweet, averaging 18 brix.
*Aroma.*—Slight.
*Eating quality.*—Very good.

STONE

Type: Clingstone.
Form: Oval.
Base: Straight.
Apex: Acute with an average angle of 90 degrees.
Side: Equal.
Surface: Slightly rough.
Ridges: None.
Color: Light brown [57. l.Br] when first removed from fresh fruit.
Average pit wall thickness: 1/16" [1.6 mm.].
Average width: 3/4" [19.1 mm.].
Average length: 1 1/16" [27.0 mm.].
Average breadth: 3/8" [9.5 mm.].
Tendency to split: Very slight.
Kernel:
*Form.*—Oval.
*Skin color.*—Light orange yellow [70. l.OY] when first removed from fresh fruit.
*Pellicle color.*—Light brown [57. l.Br].
*Taste.*—Bitter.
*Vein color.*—Light brown [57. l.BR].
*Viable.*—Yes.
*Average width.*—15/32" [11.9 mm.].
*Average length.*—9/16" [14.3 mm.].
*Amygdalin.*—Abundant.

USE

Market: Fresh and long distance shipping.
Keeping quality: Fruit quality observed to remain in good condition in excess of 30 days in standard cold room at 36° Fahrenheit [2° Celsius].
Resistance to insects: No unusual susceptibilities noted.
Resistance to diseases: No unusual susceptibilities noted.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is most similar to 'Fortune' (unpatented) by producing red plums that harvest in July, but is distinguished therefrom and an improvement thereon by producing fruit that is larger in size, much sweeter in flavor, and matures about 8 days earlier.

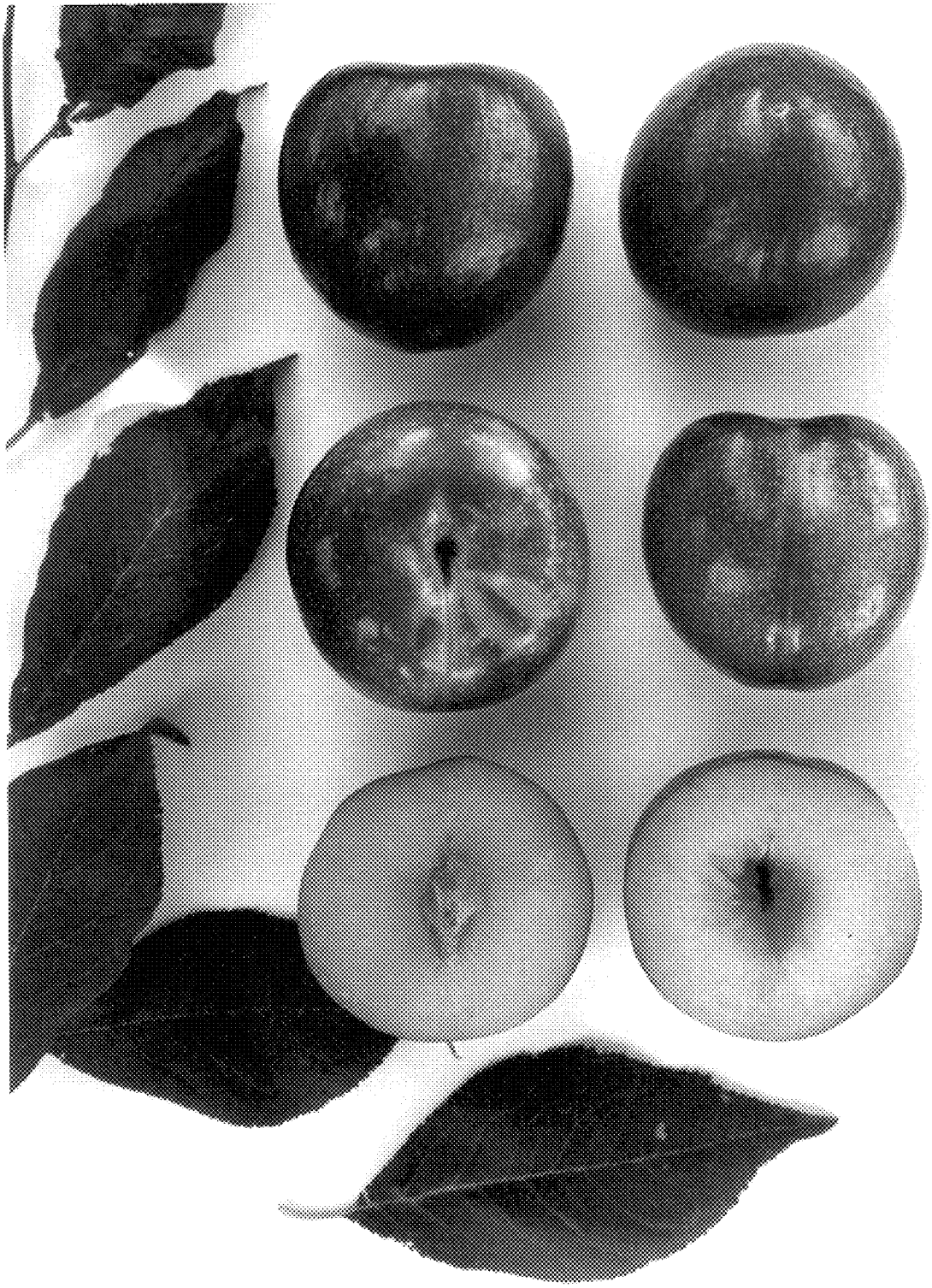

* * * * *